United States Patent [19]

Plummer

[11] 4,451,484

[45] May 29, 1984

[54] INSECTICIDAL 2,2'-BRIDGED[1,1'-BIPHENYL]-3-YLMETHYL ESTERS

[75] Inventor: Ernest L. Plummer, North Tonawanda, N.Y.

[73] Assignee: FMC Corporation, Philadelphia, Pa.

[21] Appl. No.: 368,608

[22] Filed: Apr. 15, 1982

Related U.S. Application Data

[63] Continuation-in-part of Ser. No. 259,111, Apr. 30, 1981, abandoned.

[51] Int. Cl.³ ............... C07C 69/743; C07C 69/747; A01N 53/00
[52] U.S. Cl. .................................. 424/305; 424/306; 424/308; 424/309; 560/43; 560/59; 560/105; 560/118; 560/124
[58] Field of Search ............... 560/124, 105, 118, 59, 560/43; 424/305, 306, 309, 308

[56] References Cited

U.S. PATENT DOCUMENTS

| | | | |
|---|---|---|---|
| 3,414,607 | 12/1968 | Fujimoto | 560/124 |
| 3,840,584 | 8/1974 | Crawford | 560/124 |
| 4,100,363 | 7/1978 | Bull | 424/305 |
| 4,201,787 | 5/1980 | Katsuda | 424/305 |
| 4,214,004 | 7/1980 | Plummer | 560/124 |
| 4,231,932 | 11/1980 | Martel et al. | 260/326 A |
| 4,238,505 | 12/1980 | Engel | 560/124 |

OTHER PUBLICATIONS

Johnson, J. Am. Chem. Soc., 83, pp. 417–423 (1961).
Elliott, Chem. Soc. Rev., 7, pp. 473–475 (1978).

*Primary Examiner*—Michael L. Shippen
*Attorney, Agent, or Firm*—Hansen R. L.; H. R. Ertelt

[57] ABSTRACT

2,2'-Bridged[1,1'-biphenyl]-3-ylmethyl carboxylates and insecticidal compositions containing these esters are useful for the control of a broad range of insects and acarids.

35 Claims, No Drawings

INSECTICIDAL 2,2'-BRIDGED[1,1'-BIPHENYL]-3-YLMETHYL ESTERS

This is a continuation in part of application Ser. No. 259,111 filed Apr. 30, 1981, now abandoned.

This invention pertains to the field of bioaffecting compositions; more specifically, it pertains to novel carboxylic acid esters which are pyrethroid insecticides, processes and intermediates thereto, insecticidal and acaricidal compositions containing the novel esters, and to the use of the compositions for controlling insects and acarids.

Pyrethrins have long been of interest as insecticides. Ever since it was discovered that pyrethrins are organic esters, various synthetic modifications have been made in the carboxylic acid and in the alcohol moieties on either side of the ester linkage. Many of the synthetic pyrethroids are most effective than the natural pyrethrins, and recent modifications have overcome a chronic pyrethrin problem-instability to air and light.

The carboxylic acid moiety in the aforesaid esters is often a 2,2-dimethylcyclopropane-1-carboxylic acid with various substituents in the 3-position. Many variations in the alcohol moiety of the aforesaid esters have been investigated also. U.S. Pat. No. 4,130,657 discloses that [1,1'-biphenyl]-3-ylmethyl 3-(2,2-dihaloethenyl)-2,2-dimethylcyclopropanecarboxylates, wherein the halogen is chlorine or bromine, exhibit insecticidal and acaricidal activity.

It has now been found that insecticidal and acaricidal esters result when a 2,2'-bridged[1,1'-biphenyl]-3-ylmethyl moiety is coupled with pyrethroid carboxylic acid moieties.

Like the earlier esters, several of the new pyrethroids are capable of both geometrical and optical isomerism, the biological activity varying somewhat according to the specific isomer. The pure cis geometrical isomer of a 2,2'-bridged[1,1'-biphenyl]-3-ylmethyl pyrethroid ester is usually a more active insecticide and acaricide than the pure trans isomer, and the activity of a 2,2'-bridged[1,1'-biphenyl]-3-ylmethyl pyrethroid ester is a function of the cis/trans ratio.

Although, in general, the preparation and testing of racemic esters is described specifically below, the pure optical isomers also display biological activity in varying degrees. The terms "2,2'-bridged[1,1'-biphenyl]-3-ylmethyl pyrethroid ester" or "2,2'-bridged[1,1'-biphenyl]-3-ylmethyl carboxylate" employed herein are intended to include generically all optical and geometrical isomers of the named compounds and mixtures thereof. The terms "halo," "halogen," or "halide" mean fluorine, chlorine or bromine. The term "lower" modifying alkyl or alkoxy means $C_1$ to $C_6$, preferably $C_1$ to $C_4$.

Insecticidal and acaricidal 2,2'-bridged[1,1'-biphenyl]-3-methyl pyrethroid esters of this invention are represented by Formula I

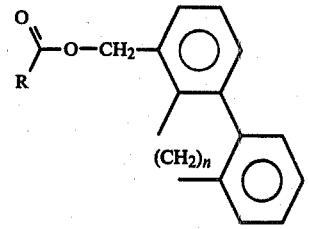

wherein n is 1–4 and R is a pyrethroid acid residue, i.e., the residue of a carboxylic acid which forms an insecticidal ester with 3-phenoxybenzyl alcohol.

Attractive pyrethroid acid residues include 3-(2,2-dihaloethenyl)-2,2-dimethylcyclopropyl, especially 3-(2,2-dichloroethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(1,2,2,2-tetrabromoethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 4-chloro-α-(1-methylethyl)phenylmethyl; 4-difluoromethoxy-α-(1-methylethyl)phenylmethyl; 3-(1,3-butadienyl)-2,2-dimethylcyclopropyl; 2,2-dimethyl-3-(oximinomethyl)cyclopropyl; 2-(2-chloro-α,α,α-trifluoro-p-toluidino)-3-methylbutyl; 3-(2,3,4,5-tetrahydro-2-oxothien-3-ylidenemethyl)-2,2-dimethylcyclopropyl; 2,2-dichloro-1-(4-ethoxyphenyl)cyclopropyl; 4-halo-α-(1-cyclopropyl)phenylmethyl; spiro[2,2-dimethylcyclopropane-1,1'-[1H]-indene]-3-yl; spiro[3-(2,2-dichloroethenyl)cyclopropane-1,1'-cyclohexane]-2-yl; spiro[3-(2,2-dichloroethenyl)cyclopropane-1,1'-cyclobutane]-2-yl; 3-phenyl-2,2-dimethylcyclopropyl; 3-(4-halophenyl)-2,2-dimethylcyclopropyl; 3-(4-methoxyphenyl)-2,2-dimethylcyclopropyl; 3-(4-ethoxyphenyl)-2,2-dimethylcyclopropyl; and 3-(3,4-methylenedioxyphenyl)-2,2-dimethylcyclopropyl.

Among the aforesaid prethroid acid residues, those that are especially attractive include 3-(2,2-dihaloethenyl)-2,2-dimethylcyclopropyl, especially 3-(2,2-dichloroethenyl)-2,2-dimethylcyclopropyl and 3-(2,2-dibromoethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 3-(1,2,2,2-tetrabromoethyl)-2,2-dimethylcyclopropyl; 2,2-dichloro-1-(4-ethoxyphenyl)cyclopropyl; 2-(2-chloro-α,α,α-trifluoro-p-toluidino)-3-methylbutyl; and 4-chloro-α-(1-methylethyl)phenylmethyl.

Among the aforesaid esters it is preferred that n be 2 or 3 and that R be either 3-(2,2-dichloroethenyl)-2,2-dimethylcyclopropyl or 3-(2-chloro-3,3,3-trifluoro-1-propenyl)-2,2-dimethylcyclopropyl. An especially attractive insecticide and acaricide is (6,7-dihydro-5H-dibenzo[a,c]cyclohepten-4-yl)methyl 3-(2-chloro-3,3,3-trifluoro-1-propenyl)-2,2-dimethylcyclopropanecarboxylate, wherein n is 3, particularly the cis isomer.

Also within the contemplation of this invention are insecticidal and acaricidal compositions comprising an insecticidally or acaricidally effective amount of 2,2'-bridged[1,1'-biphenyl]-3-ylmethyl pyrethroid ester in admixture with an agriculturally acceptable carrier and a method of controlling insects or acarids which comprises applying to the locus where control is desired an insecticidally or acaricidally effective amount of 2,2'-bridged-[1,1'-biphenyl]-3-ylmethyl pyrethroid ester.

When the locus is soil, e.g. soil in which agricultural crops are planted, it may be advantageous to incorporate the 2,2'-bridged[1,1'-biphenyl]-3-ylmethyl pyrethroid ester into the soil. This is especially effective in controlling certain pests, such as southern corn rootworm. (5,6,7,8-Tetrahydrodibenzo[a,c]cycloocten-4-yl)methyl 3-(2-chloro-3,3,3-trifluoropropenyl)-2,2-dimethylcyclopropanecarboxylate, (5,6,7,8-tetrahydrodibenzo[a,c]cycloocten-4-yl)methyl 3-(2,2-dichloroethenyl)-2,2-dimethylcyclopropanecarboxylate, (6,7-dihydro-5H-dibenzo[a,c]cyclohepten-4-yl)methyl 2,2-dichloro-1-(4-ethoxyphenyl)cyclopropanecarboxylate, (6,7-dihydro-5H-dibenzo[a,c]cyclohepten-4-yl)methyl 2-(2-chloro-α,α,α-trifluoro-p-toluidino)-3-methylbutyrate, (6,7-dihydro-5H-dibenzo[a,c]cyclohepten-4-yl)methyl 3-(2,2-dichloroethenyl)-2,2-dimethylcyclopropanecarboxylate, (6,7-dihydro-5H-dibenzo[a,c]cyclohepten-4-yl)methyl 3-(2,2-dibromoethenyl)-2,2-dimethylcyclopropanecarboxylate, (6,7-dihydro-5H-dibenzo[a,c]cyclohepten-4-yl)methyl 3-(1,2-dibromo-2,2-dichloroethyl)-2,2-dimethylcyclopropanecarboxylate, (6,7-dihydro-5H-dibenzo[a,c]cyclohepten-4-yl)methyl 2,2,3,3-tetramethylcyclopropanecarboxylate, (6,7-dihydro-5H-dibenzo[a,c]cyclohepten-4-yl)methyl 2,2-dichloro-3,3-dimethylcyclopropanecarboxylate, (6,7-dihydro-5H-dibenzo[a,c]cyclohepten-4-yl)methyl 3-(3-chloro-2,3,3-trifluoro-1-propenyl)-2,2-dimethylcyclopropanecarboxylate, and (6,7-dihydro-5H-dibenzo[a,c]cyclohepten-4-yl)methyl 3-(2-chloro-3,3,3-trifluoro-1-propenyl)-2,2-dimethylcyclopropanecarboxylate, for example, are active against southern corn rootworm when employed in this manner.

In comparison with the commercial pyrethroid insecticide, 3-phenoxybenzyl (±)-cis, trans-3-(2,2-dichloroethenyl)-2,2-dimethylcyclopropanecarboxylate (cis/trans 45/55), pyrethroid esters of this invention are as much as about 70 times more active, depending upon the specific ester and insect, and also exhibit better residual activity. The (6,7-dihydro-5H-dibenzo[a,c]cyclohepten-4-yl)methyl esters display systemic insecticidal activity.

The 2,2'-bridged[1,1'-biphenyl]-3-ylmethyl pyrethroid esters of this invention are prepared by reaction between a carbonyl halide, e.g. a chloride, RCOCl, wherein R is a pyrethroid acid residue; an acid, RCOOH; an ester, RCOOR', wherein R' is conveniently a $C_1$-$C_6$ alkyl group; an anhydride, RCOOR", wherein R" is $C_1$-$C_6$ alkylcarbonyl, or $C_1$-$C_6$ alkyl or aryl sulfonyl; or a nitrile, RCN, and an appropriate 2,2'-bridged[1,1'-biphenyl]-3-methanol. Alternatively, they are prepared by reacting a salt, RCOOM, where M is an alkali or alkaline earth metal, e.g., Li, K, Na, Ca, or Mg, a transition metal, e.g., Ag, or ammonium or alkyl-substituted ammonium, with a 2,2'-bridged[1,1'-biphenyl]-3-ylmethyl compound wherein the benzylic carbon atom carries a leaving group which is readily displaced by carboxylate anions. Suitable leaving groups are known in the art and include, for example, halogen, especially bromine and chlorine; carboxylate, especially acetate; sulfonate, e.g.,

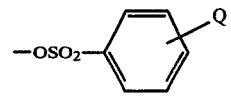

where Q is halogen, especially bromine, $C_1$-$C_6$ alkyl, e.g., p-toluenesulfonate, nitro, or hydrogen, and —O-$SO_2C_RH_SF_T$ where R is 1-4, e.g., methanesulfonate, and S and T are independently 0-9; and —$NR_3X$, where R may be $C_1$-$C_6$ alkyl, and X may be halogen, sulfonate, or other readily available anion.

3-(2,2-Dichloroethenyl)- and 3-(2,2-dibromoethenyl)-2,2-dimethylcyclopropanecarboxylic acid and corresponding carbonyl chlorides are obtained by methods disclosed in U.S. Pat. No. 4,024,163. Carbonyl chlorides or corresponding salts wherein R is 2,2,3,3-tetramethylcyclopropyl, 2,2-dichloro-3,3-dimethylcyclopropyl, 3-cyclopentylidenemethyl-2,2-dimethylcyclopropyl, and 4-chloro-α-(1-methylethyl)phenylmethyl, are disclosed in Agr. Biol. Chem., 31, 1143 (1967), Agr. Biol. Chem., 38, 1511 (1974), U.S. Pat. No. 3,679,667, and Agr. Biol. Chem., 39, 267 (1975), respectively. The 3-(2-methyl-1-propenyl)-2,2-dimethylcyclopropyl, 3-(1,2-dibromo-2,2-dichloroethyl)-2,2-dimethylcyclopropyl, and the set of 3-(2-chloro-3,3,3-trifluoro-1-propenyl)-2,2-dimethylcyclopropyl, 3-(3-chloro-2,3,3-trifluoro-1-propenyl)-2,2-dimethylcyclopropyl, and 3-(2,3-dichloro-3,3-difluoro-1-propenyl)-2,2-dimethylcyclopropyl acid residues are described in Agr. Biol. Chem., 28, 27 (1961), and U.S. Pat. No. 4,179,575, respectively. The 4-difluoromethoxy-α-(1-methylethyl)phenylmethyl acid residue is disclosed in Agr. Biol. Chem., 38 881 (1974), while Pestic. Sci., 7, 499 (1976) describes 3-(1,3-butadienyl)-2,2-dimethylcyclopropyl. U.S. Pat. No. 3,922,269, Pestic. Sci., 11, 224 (1980), and U.S. Pat. No. 3,842,177 disclose 2,2-dimethyl-3-(oximinomethyl)cyclopropyl, 2-(2-chloro-α,α,α-trifluoro-p-toluidino)-3-methylbutyl, and 3-(2,3,4,5-tetrahydro-2-oxothien-3-ylidenemethyl)-2,2-dimethylcyclopropyl, respectively. Nature, 272, 734 (1978) describes 2,2-dichloro-1-(4-ethoxyphenyl)cyclopropyl. The spiro[2,2-dimethylcyclopropane-1,1'-[1H]indene]-3-yl acid residue appears in Adv. Pestic. Sci., Plenary Lect. Symp. Paper Int. Congr. Pestic. Chem., 4th 1978, 2, p. 190. The remaining spiro acid residues are disclosed in "Synthetic Pyrethroids," ACS Symposium Series No. 42, Washington, D.C., 1977, page 37, while the 3-phenyl and substituted phenyl-2,2-dimethylcyclopropyl acid residues have been described by Farkas and Novak, Coll. Czech. Chem. Comm., 25, 1815 (1960). The 4-halo-α-(1-cyclopropyl)phenylmethyl acid residues appear in Abstracts, Fourth International Congress of Pesticide Chemistry, Zurich, 1978. The 3-(1,2,2,2-tetrabromoethyl)-2,2-dimethylcyclopropyl acid residue is described in U.S. Pat. No. 4,231,932. These disclosures are also incorporated herein by reference.

The pure cis or trans cyclopropanecarboxylates are prepared either by reacting pure cis or pure trans cyclopropanecarboxylic acid derivatives with appropriate 2,2'-bridged[1,1'-biphenyl]-3-ylmethyl compounds or by separating cis,trans mixtures using chromatographic techniques. The identities of the cis and trans isomers are established by reference to their nmr spectra, especially the patterns at 5.44–5.71 ppm and 6.10–6.40 ppm for the trans and cis isomers, respectively.

2,2'-Bridged[1,1'-biphenyl]-3-ylmethyl compounds, which are intermediate in the preparation of many of the insecticidal esters, are novel compositions of matter and are also within the scope of this invention. These intermediates are described by Formula II

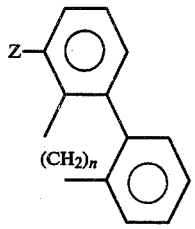

II wherein Z is Y—CH$_2$— or R$_1$, and (1) when Z is Y—CH$_2$—, n is 1–4, and Y is hydroxyl or a leaving group readily displaced by carboxylate anions, with the proviso that n is 2–4 when Y is hydroxyl, and (2) when Z is R$_1$, n is 2–4, and R$_1$ is lower alkoxycarbonyl; or n is 3–4, and R$_1$ is halogen (preferably chlorine), cyano, hydroxycarbonyl, or chlorocarbonyl. The intermediate 9H-fluorene-1-methanol, is known; *J. Am. Chem. Soc.*, 83, 417 (1961).

Intermediates within the scope of this invention include, for example, 9,10-dihydrophenanthrene-1-methanol, 6,7-dihydro-5H-dibenzo[a,c]cycloheptene-4-methanol, and 5,6,7,8-tetrahydrodibenzo[a,c]cycloocten-4-methanol. A 2,2'-bridged[1,1'-biphenyl]-3-methyl alcohol can be converted into the corresponding 2,2'-bridged[1,1'-biphenyl]-3-ylmethyl bromide by treating a solution of the alcohol in ether with phosphorous tribromide or phosphorous pentabromide. Similarly, a 2,2'-bridged[1,1-biphenyl]-3-ylmethyl bromide can be converted into the corresponding alcohol by first treating the bromide with sodium acetate in acetic acid, and then treating the thus produced biphenyl acetate with sodium hydroxide in methanol. In general, a 3-chloromethyl compound is prepared by treating the corresponding [1,1'-biphenyl]-3-methanol with thionyl chloride. The corresponding 3-methyl methanesulfonate or 3-methyl p-toluenesulfonate is prepared by treating the 3-methanol with methanesulfonyl chloride or p-toluenesulfonyl chloride, respectively. These techniques are available in the prior art, as are methods for preparing the other intermediates of Formula II.

Preparation of specific compounds within the scope of this invention is illustrated below. Unless otherwise indicated, all temperatures are in degrees Celsius and pressures are in millimeters of mercury. Proton chemical shifts, taken from nmr spectra in CDCl$_3$, are reported in ppm with respect to tetramethylsilane.

EXAMPLE A 9,10-Dihydrophenanthrene-1-methanol

A stirred mixture of ethyl 2-methylbenzoate (30 grams, 0.183 mole) and N-bromosuccinimide (35 grams, 0.194 mole) in carbon tetrachloride (200 ml) was irradiated with an infrared lamp and heated at reflux for 20 minutes. The reaction mixture was allowed to cool to room temperature, then filtered. The filtrate was evaporated under reduced pressure to give ethyl 2-bromomethylbenzoate as a yellow oil.

A stirred solution of ethyl 2-bromomethylbenzoate (44 grams, 0.18 mole) and triphenylphosphine (50 grams, 0.19 mole) in chloroform (200 ml) was heated on a steam bath for one hour, then allowed to stand at room temperature for approximately 18 hours. The mixture was diluted with diethyl ether to separate an oil which crystallized. The crystals were collected by filtration and dried under reduced pressure to give 2-(1-oxopropoxy)phenylmethyl triphenylphosphonium bromide.

Under a dry nitrogen atmosphere 2-nitrobenzaldehyde (15 grams, 0.1 mole) and 1,4,7,10,13,16-hexaoxacyclooctadecane (0.05 gram) were added to a stirred mixture of 2-(1-oxopropoxy)phenylmethyl triphenylphosphonium bromide (52.5 grams, 0.1 mole) and potassium carbonate (14 grams, 0.11 mole) in tetrahydrofuran (250 ml). The mixture was heated at reflux for three days, then allowed to stand at room temperature for five days. The mixture was evaporated under reduced pressure to give a residue, which was extracted with several portions of hot petroleum ether. The extracts were combined and evaporated under reduced pressure to give ethyl 2-[2-(2-nitrophenyl)ethenyl]benzoate as a yellow solid.

Hydrogenation of ethyl 2-[2-(2-nitrophenyl)ethenyl]benzoate (20 grams, 0.067 mole) with 5% palladium on charcoal (1 gram), ethanol (100 ml), and ethylacetate (100 ml) in a Parr hydrogenator (30–40 lb of hydrogen pressure) gave ethyl 2-[2-(2-aminophenyl)ethenyl]benzoate as a yellow oil.

To a stirred solution of ethyl 2-[2-(2-aminophenyl)ethenyl]benzoate (13.5 grams, 0.05 mole) in warm glacial acetic acid (75 ml) was added a solution of concentrated hydrochloric acid (12 ml) in water (10 ml). The mixture was cooled to 0°, and during a 20 minute period a solution of sodium nitrite (3.7 grams, 0.054 mole) in water (30 ml) was added. The resultant mixture was stirred at 0°–5° for three hours. During a 90 minute period the mixture was added to a refluxing solution of copper sulfate (35 grams, 0.14 mole) in water (500 ml). After complete addition, glacial acetic acid (40 ml) was added and the mixture refluxed for one hour. The mixture was cooled to room temperature and extracted with three 200 ml portions of methylene chloride. The extracts were combined, washed with water, and evaporated under reduced pressure to give a brown oil. Distillation of the oil under reduced pressure gave ethyl 9,10-dihydrophenanthrene-1-carboxylate (5.5 grams, bp 145°–165°/0.25 mm) as a yellow oil.

Under a dry nitrogen atmosphere a solution of ethyl 9,10-dihydrophenanthrene-1-carboxylate (5.15 grams, 0.02 mole) in anhydrous diethyl ether (50 ml) was added to a slurry of lithium aluminum hydride (0.5 grams, 0.013 mole) in anhydrous diethyl ether (100 ml). The rate was such that a reflux was maintained throughout the addition. After complete addition, the mixture was stirred at room temperature for two hours. Water (1 ml) was cautiously added to the reaction mixture, followed by 10% aqueous sodium hydroxide (1 ml) and water (3 ml). Diatomaceous earth was added to the mixture and the resultant mixture filtered. The filter cake was washed with diethyl ether and the filtrates combined and evaporated under reduced pressure to give a green solid. This solid was chromatographed on silica gel using methylene chloride as eluant to give a brown solid. Recrystallization from n-hexane gave 9,10-dihydrophenanthrene-1-methanol (1.5 grams) as tan crystals (mp 108°–110°).

Analysis: nmr(δ): 1.8(bs,1H); 2.98(s,4H); 4.83(s,2H); 7.28–7.88(m,7H).

EXAMPLE B 6,7-Dihydro-5H-dibenzo[a,c]cycloheptene-4-methanol

Under a dry nitrogen atmosphere isoamyl nitrite (37 grams, 0.31 mole) was added to a stirred solution of 3-chloro-2-methylaniline (35 grams, 0.25 mole) in benzene (500 ml). The mixture was heated at reflux for 1.5 hours, then allowed to cool and stirred at 50° for approximately 18 hours. The reaction mixture was cooled to room temperature, then evaporated under reduced pressure to a red residue. The residue was distilled under reduced pressure to give a yellow oil (bp 115°–130°/0.9 mm). The pot residue was washed with chloroform and the distillate dissolved in chloroform. The chloroform fractions were combined, washed with 10% aqueous hydrochloric acid and evaporated to give 3-chloro-2-methyl[1,1'-biphenyl] as a yellow oil.

A mixture of 3-chloro-2-methyl[1,1'-biphenyl] (10.4 grams, 0.051 mole) and N-bromosuccinimide (9.2 grams, 0.052 mole) in carbon tetrachloride (150 ml) was heated and irradiated with an infrared lamp for two hours. The mixture was cooled and filtered. The filtrate was evaporated under reduced pressure to give a quantitative yield of 2-bromomethyl-3-chloro[1,1'-biphenyl] as a yellow oil.

Under a dry nitrogen atmosphere a stirred mixture of sodium hydride (2.58 grams of a 50% dispersion in mineral oil), N,N-dimethylformamide (25 ml) and benzene (100 ml) was cooled in an ice bath. Diethyl malonate (16 grams, 0.1 mole) was added slowly to the mixture, and the mixture was stirred for 15 minutes after complete addition. A solution of 2-bromomethyl-3-chloro[1,1'-biphenyl] (15 grams, 0.05 mole) in benzene (25 ml) was added to the reaction mixture and, after complete addition, the mixture was stirred for 1.5 hours at 0°. The mixture was then warmed to approximately 70° and stirred at that temperature for 45 minutes. The mixture was allowed to cool to room temperature and stirred for approximately 18 hours. The mixture was then partitioned between water (100 ml) and diethyl ether (100 ml), and the aqueous phase was washed twice with 50 ml portions of diethyl ether. The organic phase and washes were combined and washed successively with 100 ml portions of 5% aqueous hydrochloric acid, water, saturated aqueous sodium bicarbonate, and water. The organic phase was treated with decolorizing charcoal, dried over anhydrous magnesium sulfate, and filtered. The filtrate was evaporated under reduced pressure (40°–50°/1 mm) to give ethyl 3-(3-chloro[1,1'-biphenyl]-2-yl) [2-(1-oxopropoxy)]propionate.

A stirred solution of ethyl 3-(3-chloro[1,1'-biphenyl]-2-yl) [2-(1-oxopropoxy)]propionate (17 grams, 0.05 mole), potassium hydroxide (8.4 grams, 0.15 mole) in water (20 ml) and ethanol (80 ml) was heated at reflux. After two hours, an additional 20 ml of water was added and the reaction mixture heated at reflux for another 1.5 hours. The mixture was diluted with 10% aqueous sodium hydroxide (200 ml) and the resultant solution heated at reflux for 30 minutes. The reaction mixture was cooled and washed with two 50 ml portions of methylene chloride, then acidified with hydrochloric acid, which precipitated an oil. The mixture was extracted with four 100 ml portions of methylene chloride. The extracts were combined, washed with water, dried over anhydrous magnesium sulfate, and filtered. The filtrate was evaporated to a brown solid residue. The residue was slurried in 1:1 methylene chloride:petroleum ether and filtered to give 3-(3-chloro[1,1'-biphenyl]-2-yl) (1-carboxy)propanoic acid (mp 168°–175°).

Under a dry nitrogen atmosphere 3-(3-chloro[1,1'-biphenyl]-2-yl) (1-carboxy)propanoic acid (12.8 grams, 0.042 mole) was heated at 160°–180° for 30 minutes to give a brown oil. The oil was cooled, dissolved in chloroform, treated with decolorizing carbon and anhydrous magnesium sulfate, and filtered. The filtrate was evaporated under reduced pressure to give a quantitative yield of (3-chloro[1,1'-biphenyl]-2-yl)propanoic acid as a solid.

A stirred solution of (3-chloro[1,1'-biphenyl]-2-yl)propanoic acid (5 grams, 0.019 mole) and thionyl chloride (10 ml, 0.14 mole) was heated at reflux for one hour. The excess thionyl chloride was distilled from the mixture under reduced pressure to leave a residue. Benzene was added, then distilled to remove any residual thionyl chloride, leaving 3-(3-chloro[1,1'-biphenyl]-2-yl)propanoyl chloride as a brown liquid residue.

In a manner similar to that of W. S. Johnson and H. J. Glenn, *J. Am. Chem. Soc.*, 71, 1092 (1949), the reaction of 3-(3-chloro[1,1'-biphenyl]-2-yl)propanoyl chloride (5.3 grams, 0.019 mole), aluminum chloride (3.33 grams, 0.025 mole) and benzene (125 ml) gave a brown oil. The oil was subjected to column chromatography on silica gel and eluted with 9:1 chloroform:petroleum ether to give 8-chloro-6,7-dihydro-5H-dibenzo[a,c]cycloheptene-5-one as a solid.

Under a dry nitrogen atmosphere a stirred mixture of 8-chloro-6,7-dihydro-5H-dibenzo[a,c]cycloheptene-5-one (2.6 grams, 0.011 mole), 85% hydrazine hydrate (5 ml, 0.1 mole), potassium hydroxide (4 grams, 0.071 mole) and ethylene glycol (30 ml) was heated at reflux for 1.5 hours. Sufficient volatiles were removed by distillation to increase the pot temperature to 200° while maintaining reflux. The two-phase reaction mixture was refluxed at that temperature for three hours. The mixture was cooled, poured into ice water, and the resultant mixture extracted with diethyl ether. The extract was washed with water, dried over anhydrous magnesium sulfate, and filtered. The filtrate was evaporated under reduced pressure to give a yellow oil. The oil was purified by distillation to give 4-chloro-6,7-dihydro-5H-dibenzo[a,c]cycloheptene (bp 119°–126°/0.15 mm). Under a dry nitrogen atmosphere a mixture of 4-chloro-6,7-dihydro-5e,uns/H/ -dibenzo[a,c]cycloheptene (1.6 grams, 0.007 mole), cuprous cyanide (0.95 gram, 0.011 mole), and pyridine (0.8 gram, 0.01 mole) was stirred and heated at 195° for approximately 16 hours. The mixture was cooled, dissolved in methylene chloride (150 ml), and the resultant solution was washed with three 70 ml portions of concentrated ammonium hydroxide. The organic phase was dried over anhydrous magnesium sulfate and filtered. The filtrate was evaporated under reduced pressure to give a brown solid. Recrystallization from n-hexane gave 6,7-dihydro-5e,uns/H/ -dibenzo[a,c]cycloheptene-4-carbonitrile (mp 109°–111°).

Under a dry nitrogen atmosphere a solution of 6,7-dihydro-5e,uns/H/ -dibenzo[a,c]cycloheptene-4-carbonitrile (2.95 grams, 0.0134 mole), potassium hydroxide (4 grams, 0.085 mole), ethylene glycol (40 ml) and water (3 ml) was heated at reflux for approximately 24 hours. The mixture was cooled, diluted with water, and the solution was washed with diethyl ether. The aqueous solution was acidified and extracted with diethyl ether. The extract was dried over anhydrous magnesium sulfate and filtered. The filtrate was evaporated to give a white solid. The solid was combined with similar material prepared in a separate experiment, and the combined solids were recrystallized from n-hexane to give 6,7-dihydro-5H-dibenzo[a,c]cycloheptene-4-carboxylic acid (mp 137°-139°) as nearly white crystals.

Under a dry nitrogen atmosphere a stirred solution of 6,7-dihydro-5H-dibenzo[a,c]cycloheptene-4-carboxylic acid (3.4 grams, 0.0142 mole) in thionyl chloride (10 ml) was heated at reflux for 1.5 hours. The excess thionyl chloride was removed by distillation under reduced pressure. Benzene (10 ml) was added and then removed by distillation under reduced pressure to leave 6,7-dihydro-5H-dibenzo[a,c]cycloheptene-4-carbonyl chloride as a residue.

The reaction of 6,7-dihydro-5H-dibenzo[a,c]cycloheptene-4-carbonyl chloride (3.5 grams, 0.014 mole), lithium aluminum hydride (0.6 grams, 0.016 mole), and diethyl ether (100 ml) gave a yellow oil. The oil was dissolved in methanol/water, and the solution was extracted with diethyl ether. The extract was dried over anhydrous magnesium sulfate and filtered. The filtrate was evaporated to give 6,7-dihydro-5H-dibenzo[a,c]cycloheptene-4-methanol as a yellow oil.

Analysis: nmr($\delta$): 2.12–2.58(m,7H); 4.9(s,2H); 7.28–7.50(m,7H).

EXAMPLE C 5,6,7,8-Tetrahydrodibenzo[a,c]cycloocten-4-methanol

Under a dry argon atmosphere, borane-tetrahydrofuran complex (230 ml of a 1.5 M solution in tetrahydrofuran) was added dropwise to a stirred solution of (3-chloro[1,1'-biphenyl]-2-yl)propanoic acid (40.0 g, 0.15 mole) in tetrahydrofuran (250 ml). The reaction mixture was stirred at room temperature for approximately 18 hours. Water (30 ml) was then added to the reaction mixture during a 0.5 hour period. The solvent was removed from the mixture under reduced pressure to yield an oil. The oil was partitioned between methylene chloride and dilute aqueous sodium hydroxide. The organic phase was separated, dried over anhydrous magnesium sulfate, filtered and the filtrate evaporated under reduced pressure to yield 3-(3-chloro[1,1'-biphenyl]-2-yl)-1-propanol as an oil.

Analysis calc'd for $C_{15}H_{15}ClO$: C 73.02; H 6.12; Found: C 73.00; H 6.50.

The IR and nmr spectra were consistent with the proposed structure.

A stirred solution of 3-(3-chloro[1,1'biphenyl]-2-yl)-1-propanol (30.0 g, 0.12 mole) and pyridine (11.9 g, 0.15 mole) in methylene chloride (300 ml) was cooled to 0°. Methanesulfonyl chloride (13.9 g, 0.12 mole) was added dropwise to the mixture. After complete addition the mixture was allowed to warm to room temperature and stir for approximately 18 hours. The reaction mixture was diluted with ice water (50 grams) and washed successively with dilute hydrochloric acid (200 ml), saturated aqueous sodium chloride (700 ml) and dilute aqueous sodium hydroxide (200 ml). The organic phase was dried over anhydrous magnesium sulfate, filtered and the filtrate evaporated under reduced pressure to yield (3-chloro[1,1'-biphenyl]-2-yl)propanyl methylsulfonate as a brown oil.

Analysis calc'd for $C_{16}H_{17}ClO_3S$: C 59.17; H 5.27; Found: C 59.70; H 5.41.

The IR and nmr spectra were consistent with the proposed structure.

In a manner similar to that of Bloomfield and Fennessey, Tett. Letters No. 33, 2273–2276 (1964), the reaction of (3-chloro[1,1'-biphenyl]-2-yl)propanyl methylsulfonate (4.8 g, 0.015 mole), sodium cyanide (2.2 g, 0.44 mole), and dimethyl sulfoxide (35 ml) produced an oil. The oil was subjected to column chromatography on silica gel, eluted with toluene, to give 4-(2-chloro[1,1'biphenyl]-2-yl)butanenitrile as a clear oil. The IR and nmr spectra were consistent with the proposed structure.

A stirred solution of 4-(2-chloro[1,1'-biphenyl]-2-yl)butanenitrile (2.7 g, 0.011 mole), potassium hydroxide (6.9 g, 0.11 mole), and ethylene glycol (25 ml) in water (25 ml) was heated at reflux for approximately 18 hours. The reaction mixture was cooled to room temperature, diluted with ice water (100 g) and acidified with concentrated hydrochloric acid. The mixture was saturated with sodium chloride, then extracted with diethyl ether (three 100 ml portions) and methylene chloride (100 ml). The extracts were combined, dried over anhydrous magnesium sulfate, filtered and the filtrate evaporated under reduced pressure to yield 4-(3-chloro[1,1'-biphenyl]-2-yl)butanoic acid as a solid (m.p. 74°-76°).

Analysis calc'd for $C_{16}H_{15}ClO_2$: C 69.95; H 5.50; Found: C 70.64; H 5.85.

The IR and nmr spectra were consistent with the proposed structure.

Under a dry argon atmosphere a stirred solution of 4-(3-chloro[1,1'-biphenyl]-2-yl)butanoic acid (22.8 g, 0.083 mole) in toluene (500 ml) was heated at 65°. Oxalyl chloride (21 g, 0.166 mole) was added slowly to the reaction mixture. After complete addition the mixture was allowed to stir at 40° for approximately 18 hours. The solvent and excess oxalyl chloride were removed by distillation under reduced pressure. Further distillation under reduced pressure gave 4-(3-chloro[1,1'-biphenyl]-2-yl)butanoic acid chloride (b.p. 150°/0.04 mm) as a clear oil. The nmr spectrum was consistent with the proposed structure.

Using the extreme-dilution technique described by Hedden and Brown, J. Am. Chem. Soc., 75, 3744-48 (1953), 4-(3-chloro-[1,1'-biphenyl]-2-yl)butanoic acid chloride (18.9 g, 0.069 mole) was diluted in carbon disulfide (100 ml) and placed in the dropping funnel. The dilution flask was filled with carbon disulfide (approximately 700 ml). Aluminum chloride (19.8 g, 0.15 mole) in carbon disulfide (700 ml) was placed in the reaction flask and heated at reflux. The contents of the dropping funnel were added to the reaction during an eight day period. After complete addition the contents of the dilution flask were added to the reaction flask and the mixture allowed to stir at room temperature for approximately 18 hours. One liter of 2 N hydrochloric acid was added to the mixture and the total stirred for 0.5 hour. The mixture was poured into a separatory funnel and the organic phase separated. The remaining aqueous phase was saturated with sodium chloride and extracted with methylene chloride (3×250 ml). The organic phase and extracts were combined, dried over anhydrous magnesium sulfate, filtered and the filtrate evaporated under reduced pressure to yield an oil. The oil was subjected to column chromatography on silica gel eluted with toluene:methylene chloride (1:1). The fractions which contained the desired product were combined and evaporated under reduced pressure to give a solid. The solid was recrystallized from methylcyclohexane:n-heptane (30:70) to yield 9-chloro-5,6,7,8-tetrahydrodibenzo[a,c]cycloocten-5-one (m.p. 117.5°-118.5°). The solvent was evaporated from the mother liquor to give an oil. This oil was subjected to column chromatography on silica gel eluted with n-heptane:ethyl acetate (40:1). The fractions which contained the desired product were combined and evaporated under reduced pressure to give additional product.

Analysis calc'd for $C_{16}H_{13}ClO$: C 74.86; H 5.10; Found: C 74.66; H 4.85.

The IR, nmr and mass spectra were consistent with the proposed structure.

The reaction of 9-chloro-5,6,7,8-tetrahydrodibenzo[a,c]cycloocten-5-one (3.0 g, 0.015 mole), 85% hydrazine hydrate (4.5 g, 0.076 mole), potassium hydroxide (3.0 g, 0.046 mole) and ethylene glycol (39 ml) produced an oil. The oil was purified by column chromatography on silica gel, eluted with toluene to yield 4-chloro-5,6,7,8-tetrahydrodibenzo[a,c]cyclooctene as an oil (3.3 grams).

Analysis calc'd for $C_{16}H_{15}Cl$: C 79.17; H 6.22; Found: C 78.88; H 6.58.

The IR and nmr spectra were consistent with the proposed structure.

The reaction of 4-chloro-5,6,7,8-tetrahydrodibenzo[a,c]cyclooctene (3.3 g, 0.014 mole), cuprous cyanide (2.44 g, 0.027 mole) and pyridine (2.5 g, 0.027 mole) produced 5,6,7,8-tetrahydrodibenzo[a,c]cycloocten-4-carbonitrile as an oil (60% product, 40% starting material by gas chromatography). The IR spectrum possessed an adsorption at $4.45\mu$ indicating a CN group.

Under a dry nitrogen atmosphere a solution of the oil just described (3.0 g), potassium hydroxide (7.2 g, 0.128 mole), ethylene glycol (30 ml) and water (30 ml) was heated at reflux for 24 hours. The reaction mixture was cooled to room temperature and transferred to a separatory funnel. The reaction flask was washed successively with water (150 ml), diethyl ether (150 ml), 2 N hydrochloric acid (150 ml) and the washes added to the separatory funnel. Ice was added to the separatory funnel. The contents of the separatory funnel were made acidic with concentrated hydrochloric acid, then shaken well. A white solid formed, was removed from the mixture by filtration and found to be 5,6,7,8-tetrahydrodibenzo[a,c]cycloocten-4-carboxamide (compound A). An aqueous phase was separated from the filtrate and extracted with diethyl ether (three 100 ml portions) (Extracts B). The extracts (Extracts B) were combined and evaporated under reduced pressure to leave a solid. The solid was dissolved in methylene chloride (200 ml) and the solution (Solution C) washed with 2 N sodium hydroxide (two 125 ml portions) (basic washes D). The basic washes (basic washes D) were combined and back washed with methylene chloride (100 ml) (organic wash E, basic aqueous phase F). The organic phases (solution C, wash E) were combined, dried over anhydrous sodium sulfate and filtered. The filtrate was evaporated under reduced pressure to yield a solid which consisted of 5,6,7,8-tetrahydrodibenzo[a,c]cycloocten-4-carboxamide and 5,6,7,8-tetrahydrodibenzo[a,c]cycloocten-4-carbonitrile (compound G). The basic aqueous phase (basic aqueous phase F) was acidified with concentrated hydrochloric acid and the solution saturated with sodium chloride. The saturated solution was extracted with diethyl ether (two 200 ml portions). The extracts were combined, dried over anhydrous magnesium sulfate and filtered. The filtrate was evaporated under reduced pressure to yield a small amount of 5,6,7,8-tetrahydrodibenzo[a,c]cycloocten-4-carboxylic acid. All portions of carbonitrile and carboxamide, which were isolated above (compounds A, G) were combined and treated with potassium hydroxide (7.7 g) and ethylene glycol (50 ml) at 150° for approximately 18 hours. The reaction mixture was cooled to room temperature, transferred to a separatory funnel and treated as above. After the contents of the separatory funnel were acidified and shaken, the aqueous phase was separated from the mixture. The aqueous phase was extracted with diethyl ether and evaporated under reduced pressure to leave a residue. The residue was dissolved in methylene chloride and the solution extracted with 2 N sodium hydroxide. The aqueous extract was washed with methylene chloride, then acidified with concentrated hydrochloric acid and saturated with sodium chloride. The saturated solution was extracted with diethyl ether. The extract was dried over anhydrous magnesium sulfate and filtered. The filtrate was evaporated under reduced pressure to give 5,6,7,8-tetrahydrodibenzo[a,c]cycloocten-4-carboxylic acid as a solid (1.7 g) (m.p. 178°-180°). The IR and nmr spectra were consistent with the proposed structure.

A preferred method of preparation is by the method wherein the oil, potassium hydroxide and ethylene glycol (no water) are heated at reflux for 18 to 24 hours.

The reaction between 5,6,7,8-tetrahydrodibenzo[a,c]cycloocten-4-carboxylic acid (1.7 g, 0.0067 mole) and borane-tetrahydrofuran complex (1.16 g of a 1.05 M solution in tetrahydrofuran) in tetrahydrofuran (50 ml) produced 5,6,7,8-tetrahydrodibenzo[a,c]cycloocten-4-methanol as an oil (1.38 g). The IR and nmr spectra were consistent with the proposed structure.

Analysis: nmr($\delta$): 1.23–3.13(m,8H); 1.83(s,1H); 4.82(s,2H); 7.13–7.57(m,7H).

Example I (9,10-Dihydro-1-phenanthryl)methyl 3-(2,2-dichloroethenyl)-2,2-dimethylcyclopropanecarboxylate A mixture of 9,10-dihydrophenanthrene-1-methanol (0.5 gram, 0.0024 mole) and pyridine (1 gram, 0.013 mole) in benzene (25 ml) was added to a stirred solution of cis-3-(2,2-dichloroethenyl)-2,2-dimethylcyclopropanecarbonyl chloride (0.7 gram, 0.0031 mole) in benzene (25 ml). The mixture was stirred at room temperature for 2.5 days, then partitioned between water (80 ml) and diethyl ether (50 ml). The organic phase was separated and washed consecutively with water, 10% aqueous sodium carbonate and water. The organic phase was then dried over anhydrous magnesium sulfate and filtered. The filtrate was evaporated to give a yellow oil. The oil was purified by chromatography on silica gel to give (9.10-dihydro-1-phenanthryl)methyl cis-3-(2,2-dichloroethenyl)-2,2-dimethylcyclopropanecarboxylate as an oil.

Analysis: Calc'd for $C_{23}H_{22}Cl_2O_2$: C 68.83; H 5.53; Found: C 69.04; H 5.78.

nmr($\delta$): 1.20(s,3H); 1.29(s,3H); 1.80–2.12(m,2H); 2.88(s,4H); 5.23(s,2H); 6.32–6.43(d,1H); 7.23–7.83(m,7H).

The trans ester is similarly prepared from the trans acid chloride.

Example II (9,10-Dihydro-1-phenanthryl)methyl 3-(2-chloro-3,3,3-trifluoro-1-propenyl)-2,2-dimethylcyclopropanecarboxylate In the manner of Example I, but substituting cis-3-(2-chloro-3,3,3-trifluoromethyl-1-propenyl)-2,2-dimethylcyclopropanecarbonyl chloride, (9,10-dihydro-1-phenanthryl)methyl cis-3-(2-chloro-3,3,3-trifluoromethyl-1-propenyl)-2,2-dimethylcyclopropanecarboxylate was prepared.

Analysis: Calc'd for $C_{24}H_{22}ClF_3O_2$: C 66.28; H 5.10; Found: C 66.40; H 5.00.

nmr($\delta$): 1.28(s,3H); 1.31(s,3H); 1.93–2.18(m,2H); 2.88(s,4H); 5.22(s,2H); 6.92–7.00(d,1H); 7.28–7.80(m,7H).

The trans ester is similarly prepared from the trans acid chloride.

Example III (6,7-Dihydro-5H-dibenzo[a,c]cyclohepten-4-yl)methyl 3-(2,2-dichloroethenyl)-2,2-dimethylcyclopropanecarboxylate In the manner of Example I, but substituting 6,7-dihydro-5H-dibenzo[a,c]cycloheptene-4-methanol, (6,7-dihydro-5H-dibenzo[a,c]cyclohepten-4-yl)methyl cis-3-(2,2-dichloroethenyl)-2,2-dimethylcyclopropanecarboxylate was prepared.

Analysis: Calc'd for $C_{24}H_{24}Cl_2O_2$: C 69.40; H 5.82; Found: C 69.43; H 5.90.

nmr($\delta$): 1.23(s,3H); 1.26(s,3H); 1.83–2.60(m,8H); 5.32(s,2H); 6.38–6.42(d,1H); 7.32–7.46(m,7H).

Similarly, but employing trans-3-(2,2-dichloroethenyl)-2,2-dimethylcyclopropanecarbonyl chloride, (6,7-dihydro-5H-dibenzo-[a,c]cyclohepten-4-yl)methyl trans-3-(2,2-dichloroethenyl)-2,2-dimethylcyclopropanecarboxylate was prepared.

Analysis: Calc'd for $C_{24}H_{24}Cl_2O_2$: C 69.40; H 5.82; Found: C 69.18; H 5.71.

nmr($\delta$): 1.18(s,3H); 1.32(s,3H); 1.62–2.60(m,8H); 5.35(s,2H); 5.63–5.72(d,1H); 7.23–7.50(m,7H).

Example IV (6,7-Dihydro-5H-dibenzo[a,c]cyclohepten-4-yl)methyl 3-(2-chloro-3,3,3-trifluoromethyl-1-propenyl)-2,2-dimethylcyclopropanecarboxylate In the manner of Example I, but substituting 6,7-dihydro-5H-dibenzo[a,c]cycloheptene-4-methanol and cis-3-(2-chloro-3,3,3-trifluoromethyl-1-propenyl)-2,2-dimethylcyclopropanecarbonyl chloride, (6,7-dihydro-5H-dibenzo[a,c]cyclohepten-4-yl)methyl cis-3-(2-chloro-3,3,3-trifluoromethyl-1-propenyl)-2,2-dimethylcyclopropanecarboxylate was prepared.

Analysis: Calc'd for $C_{25}H_{24}ClF_3O_2$: C 66.89; H 5.39; Found: C 66.64; H 5.13.

nmr($\delta$): 1.32(s,6H); 2.00–2.60(m,8H); 5.32(s,2H); 7.03–7.12(d,1H); 7.33–7.50(m,7H).

The trans ester is similarly prepared from the trans acid chloride.

Example V

9H-Fluorene-1-methyl 3-(2,2-dichloroethenyl)-2,2-dimethylcyclopropanecarboxylate In the manner of Example I, but substituting 9H-fluorene-1-methanol, 9H-fluorene-1-methyl cis-3-(2,2-dichloroethenyl)-2,2-dimethylcyclopropanecarboxylate was prepared.

Analysis: Calc'd for $C_{22}H_{20}Cl_2O_2$: C 68.23; H 5.21; Found: C 68.34; H 5.36.

nmr($\delta$): 1.21(s,3H); 1.30(s,3H); 1.82–2.15(m,2H); 3.88(s,2H); 5.30(s,2H); 6.39–6.55(dd,1H); 7.24–8.00(m,7H).

Similarly, but employing trans-3-(2,2-dichloroethenyl)-2,2-dimethylcyclopropanecarbonyl chloride, 9H-fluorene-1-methyl trans-3-(2,2-dichloroethenyl)-2,2-dimethylcyclopropanecarboxylate was prepared.

Analysis: Calc'd for $C_{22}H_{20}Cl_2O_2$: C 68.23; H 5.21; Found: C 68.20; H 5.41.

nmr($\delta$): 1.18(s,3H); 1.30(s3H); 1.61–2.33(m,2H); 3.92(s,2H); 5.30(s,2H); 5.55–5.65(d,1H); 7.24–7.91(m,7H).

Example VI

9H-Fluorene-1-methyl 3-(2-chloro-3,3,3-trifluoromethyl-1-propenyl)-2,2-dimethylcyclopropanecarboxylate In the manner of Example I, but substituting 9H-fluorene-1-methanol and cis-3-(2-chloro-3,3,3-trifluoromethyl-1-propenyl)-2,2-dimethylcyclopropanecarbonyl chloride, 9H-fluorene-1-methyl cis-3-(2-chloro-3,3,3-trifluoromethyl-1-propenyl)-2,2-dimethylcyclopropanecarboxylate was prepared.

Analysis: Calc'd for $C_{23}H_{20}ClF_3O_2$: C 65.64; H 4.79; Found: C 65.68; H 4.76.

nmr ($\delta$): 1.58(s,3H); 1.61(s,3H); 2.24–2.58(m,2H); 4.21(s,2H); 5.58(s,2H); 7.20–7.36(d,1H); 7.53–8.17(m,7H).

The trans ester is similarly prepared from the trans acid chloride.

Example VII (5,6,7,8-Tetrahydrodibenzo[a,c]cycloocten-4-yl)methyl 3-(2-chloro-3,3,3-trifluoropropenyl)-2,2-dimethylcyclopropanecarboxylate In the manner of Example I, but substituting 5,6,7,8-tetrahydrodibenzo[a,c]cyclooctene-4-methanol and cis-3-(2-chloro-3,3,3-trifluoropropenyl)-2,2-dimethylcyclopropanecarbonyl chloride, (5,6,7,8-tetrahydrodibenzo[a,c]cycloocten-4-yl)methyl cis-3-(2-chloro-3,3,3-trifluoropropenyl)-2,2-dimethylcyclopropanecarboxylate was prepared.

Analysis: Calc'd for $C_{26}H_{26}ClF_3O_2$: C 67.46; H 5.66; Found: C 67.10; H 6.00.

nmr ($\delta$): 1.30(s,H); 1.63–3.07(m,10H); 5.28(s,2H); 6.87–7.53(m,7H).

The trans ester is similarly prepared from the trans acid chloride.

Example VIII (5,6,7,8-Tetrahydrodibenzo[a,c]cycloocten-4-yl)methyl 3-(2,2-dichloroethenyl)-2,2-dimethylcyclopropanecarboxylate In the manner of Example I, but substituting 5,6,7,8-tetrahydrodibenzo[a,c]cyclooctene-4-methanol and 1R,cis-3-(2,2-dichloroethenyl)-2,2-dimethylcyclopropanecarbonyl chloride, (5,6,7,8-tetrahydrodibenzo[a,c]cycloocten-4-yl)methyl 1R,cis-3-(2,2-dichloroethenyl)-2,2-dimethylcyclopropanecarboxylate was prepared.

Analysis: Calc'd for $C_{25}H_{26}Cl_2O_2$: C 69.94; H 6.10; Found: C 67.06; H 6.21.

nmr (δ): 1.27–1.28(d,3H); 1.32(s,3H); 1.43–3.10(m,10H); 5.28(s,2H); 6.23–6.42(d,1H); 7.13–7.53(m,7H).

Example IX (6,7-Dihydro-5H-dibenzo[a,c]cyclohepten-4-yl)methyl 2,2-dichloro-1-(4-ethoxyphenyl)cyclopropanecarboxylate In the manner of Example I, but substituting 6,7-dihydro-5H-dibenzo[a,c]cycloheptene-4-methanol and 2,2-dichloro-1-(4-ethoxyphenyl)cyclopropanecarbonyl chloride, the title compound was prepared.

Analysis: Calc'd for $C_{28}H_{25}Cl_2O_3$: C 69.86; H 5.44; Found: C 69.57; H 5.67.

nmr (δ): 1.27–1.61(t,3H); 1.78–2.70(m,6H); 1.93–2.70(q,2H); 3.80–4.20(q,2H); 5.25(s,2H); 6.78–7.50(q,4H); 7.00–7.50(m,7H).

Example X (6,7-Dihydro-5H-dibenzo[a,c]cyclohepten-4-yl)methyl 2-(2-chloro-α,α,α-trifluoro-p-toluidino)-3-methylbutyrate A solution of potassium hydroxide (1.03 grams, 0.016 mole) in water (6.0 ml) was added to a stirred mixture of 2-(2-chloro-α,α,α-trifluoro-p-toluidino)-3-methylbutyric acid (4.62 grams, 0.016 mole, prepared by the method of C. A. Henrick, et al., Pest. Sci. 11, 224–41 (1980) in n-heptane (75.0 ml). The mixture was stirred until all the acid dissolved, at which time the water was distilled from the mixture. Additional n-heptane (50.0 ml) was added, followed by a solution of 1,4-diazobicyclo[2.2.2]octane (0.12 gram, 0.00097 mole) and (6,7-dihydro-5H-dibenzo[a,c]cycloheptene-4-yl)methyl p-methylphenylsulfonate in acetonitrile (40.0 ml). After complete addition, the mixture was stirred and heated at reflux for approximately 18 hours. The mixture was cooled, then evaporated to dryness under reduced pressure to leave a residue. The residue was partitioned between diethyl ether (250 ml) and water (150 ml) and the phases separated. The organic phase was washed in succession with aqueous 2% hydrochloric acid (two 50 ml portions), water (two 25 ml portions), aqueous 10% sodium carbonate (two 25 ml portions), and saturated aqueous sodium chloride (25 ml). The washed organic phase was dried over anhydrous magnesium sulfate, filtered and the filtrate evaporated under reduced pressure to leave an oil. The oil was purified by column chromatography on silica gel (250 grams), n-heptane:toluene (30:70) as the eluant, to yield (6,7-dihydro-5H-dibenzo[a,c]cyclohepten-4-yl)methyl 2-(2-chloro-α,α,α-trifluoro-p-toluidino)-3-methylbutyrate (4.95 grams) as an oil.

Analysis: Calc'd for $C_{28}H_{27}ClF_3NO_2$: C 67.00; H 5.42; Found: C 66.35; H 5.31.

nmr (δ): 0.97–1.10(dd,6H); 1.93–2.63(m,7H); 3.83–4.03(dd,1H); 5.03(s,1H); 5.27(s,2H); 6.53–7.57(m,10H).

By methods similar to those described above for Examples I–X, the following insecticidal and acaricidal 2,2'-bridged-[1,1'-biphenyl]-3-ylmethyl pyrethroid esters were prepared and characterized.

Example XI (6,7-Dihydro-5H-dibenzo[a,c]cyclohepten-4-yl)methyl 1R,cis-3-(2,2-dichloroethenyl)-2,2-dimethylcyclopropanecarboxylate Analysis: Calc'd for $C_{24}H_{24}Cl_2O_2$: C 69.4; H 5.82; Found: C 68.91; H 5.59.

nmr (δ): 1.20–1.25(d,6H); 1.75–2.72(m,8H); 5.20(s,2H); 6.22–6.37(dd,1H); 7.17–7.33(m,7H).

Example XII (6,7-Dihydro-5H-dibenzo[a,c]cyclohepten-4-yl)methyl 3-(2,2-dibromoethenyl)-2,2-dimethylcyclopropanecarboxylate Analysis (1R,cis isomer): Calc'd for $C_{24}H_{24}Br_2O_2$: C 57.17; H 4.80; Found: C 56.59; H 5.2.

nmr (δ): 1.23–1.27(d,6H); 1.80–2.73(m,8H); 5.23(s,2H); 6.72–6.87(dd,1H); 7.15–7.37(m,7H).

Example XIII (6,7-Dihydro-5H-dibenzo[a,c]cyclohepten-4-yl)methyl 3-(cyclopentylidenemethyl)-2,2-dimethylcyclopropanecarboxylate Analysis (1R,trans isomer): Calc'd for $C_{28}H_{32}O_2$: C 83.96; H 8.05; Found: C 83.72; H 7.98.

nmr (δ): 1.13(s,3H); 1.23–1.27(d,3H); 1.42–2.73(m,14H); 4.90–5.40(m,1H); 5.23(s,2H); 7.08–7.33(m,7H).

Example XIV (6,7-Dihydro-5H-dibenzo[a,c]cyclohepten-4-yl)methyl 3-(1,2-dibromo-2,2-dichloroethyl)-2,2-dimethylcyclopropanecarboxylate Analysis (1R,cis isomer): Calc'd for $C_{24}H_{33}Br_2Cl_2O_2$: C 50.12; H 4.21; Found: C 48.60; H 4.02.

nmr (δ): 1.18–1.23(d,3H); 1.38–1.40(d,3H); 1.83–2.73(m,8H); 5.04–5.53(m,1H); 5.20(s,2H); 7.10–7.34(m,7H).

Example XV (6,7-Dihydro-5H-dibenzo[a,c]cyclohepten-4-yl)methyl 2,2,3,3-tetramethylcyclopropanecarboxylate Analysis: Calc'd for $C_{24}H_{28}O_2$: C 82.72; H 8.10; Found: C 82.50; H 7.90.

nmr (δ): 1.18–1.27(d,12H); 1.87–2.77(m,6H); 2.37(s,1H); 5.23(s,2H); 7.15–7.38(m,7H).

Example XVI (6,7-Dihydro-5H-dibenzo[a,c]cyclohepten-4-yl)methyl α-(1-methylethyl)-4-chlorobenzeneacetate Analysis: Calc'd for $C_{27}H_{27}ClO_2$: C 77.4; H 6.50; Found: C 77.85; H 6.90.

nmr (δ): 0.63–1.08(dd,6H); 1.87–2.67(m,7H); 3.09–3.27(d,1H); 5.19(s,2H); 7.20–7.48(m,7H).

Example XVII (6,7-Dihydro-5H-dibenzo[a,c]cyclohepten-4-yl)methyl 2,2-dichloro-3,3-dimethylcyclopropanecarboxylate Analysis: Calc'd for $C_{22}H_{22}Cl_2O_2$: C 67.87; H 5.70; Found: C 67.79; H 5.92.

nmr (δ): 1.44–1.49(d,6H); 2.00–2.75(m,6H); 1.83(s,1H); 5.30(s,2H); 7.20–7.50(m,7H).

Example XVIII (6,7-Dihydro-5H-dibenzo[a,c]cyclohepten-4-yl)methyl 3-(3-chloro-2,3,3-trifluoro-1-propenyl)-2,2-dimethylcyclopropanecarboxylate Analysis (cis isomer): Calc'd for $C_{25}H_{24}ClF_3O_2$: C 66.89; H 5.39; Found: C 66.53; H 5.59.

nmr (δ): 1.30(s,6H); 1.83–2.74(m,8H); 5.23(s,2H); 5.73–6.43(dd,1H); 7.15–7.47(m,7H).

Example XIX (6,7-Dihydro-5H-dibenzo[a,c]cyclohepten-4-yl)methyl 3-(1,2,2,2-tetrabromoethyl)-2,2-dimethylcyclopropanecarboxylate Analysis (1R,cis isomer): Calc'd for $C_{24}H_{24}Br_4O_2$: C 43.41; H 3.64; Found: C 44.05; H 4.00.

nmr (δ): 1.27–1.30(d,3H); 1.42–1.45(d,3H); 1.79–2.70(m,8H); 5.07–5.37(dd,1H); 5.33(bs,2H); 7.13–7.47(m,7H).

Example XX (6,7-Dihydro-5H-dibenzo[a,c]cyclohepten-4-yl)methyl 1R,cis-3-(2-chloro-3,3,3-trifluoro-1-propenyl)-2,2-dimethylcyclopropanecarboxylate Analysis: Calc'd for $C_{25}H_{24}ClF_3O_2$: C 66.89; H 5.38; Found: C 68.97; H 5.83.

nmr (δ): 1.27–1.30(d,6H); 1.93–2.73(m,8H); 5.27(s,2H); 6.93–7.07(d,1H); 7.17–7.43(m,7H).

Example XXI (6,7-Dihydro-5H-dibenzo[a,c]cyclohepten-4-yl)methyl 1S,cis-3-(2-chloro-3,3,3-trifluoro-1-propenyl)-2,2-dimethylcyclopropanecarboxylate Analysis: Calc'd for $C_{25}H_{24}ClF_3O_2$: C 66.89; H 5.38; Found: C 67.47; H 5.64.

nmr (δ): 1.30(s,6H); 1.97–2.77(m,8H); 5.30(s,2H); 6.93–7.10(d,1H); 7.20–7.47(m,7H).

Example XXII (6,7-Dihydro-5H-dibenzo[a,c]cyclohepten-4-yl)methyl 1R-2,2-dichloro-1-(4-ethoxyphenyl)cyclopropanecarboxylate Analysis: nmr (δ): 1.27–1.50(t,3H); 1.77–2.70(m,6H); 1.93–2.70(q,2H); 3.83–4.20(q,2H); 5.27(s,2H); 6.77–7.47(q,4H); 7.10–7.47(m,7H).

In the normal use of the insecticidal and acaricidal esters of the present invention, the esters usually will not be employed free from admixture or dilution, but ordinarily will be used in a suitable formulated composition compatible with the method of application and comprising an insecticidally or acaricidally effective amount of 2,2'-bridged[1,1'-biphenyl]-3-ylmethyl carboxylate. The esters of this invention, like most pesticidal agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the esters. The granule particles are relatively large, a diameter of about 400–2500 microns typically. The particles are either impregnated with the ester from solution or coated with the ester, adhesive sometimes being employed. Granules generally contain 0.05–10%, preferably 0.5–5%, active ingredient as the insecticidally effective amount.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects and acarids contains 1 part of 2,2'-bridged[1,1'-biphenyl]-3-ylmethyl carboxylate, such as (6,7-dihydro-5H-dibenzo[a,c]cyclohepten-4-yl)methyl 3-(2-chloro-3,3,3-trifluoro-1-propenyl)-2,2-dimethylcyclopropanecarboxylate, and 99 parts of talc.

The esters of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5–50% 2,2'-bridged[1,1'-biphenyl]-3-ylmethyl carboxylate, such as (6,7-dihydro-5H-dibenzo[a,c]cyclohepten-4-yl)methyl 3-(2-chloro-3,3,3-trifluoropropenyl)-2,2-dimethylcyclopropanecarboxylate, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects and acarids contains 1.5 parts each of sodium lignosulfonate and sodium laurylsulfate as wetting agents, 25 parts of (9,10-dihydro-1-phenanthryl)methyl cis-3-(2,2-dichloroethenyl)-2,2-dimethylcyclopropanecarboxylate, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the ester with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal and acaricidal composition.

Other useful formulations include simple solutions of the active ingredient in a solvent in which it is completely soluble at the desired concentration, such as acetone or other organic solvents.

An insecticidally or acaricidally effective amount of 2,2'-bridged[1,1'-biphenyl]-3-ylmethyl carboxylate in an insecticidal or acaricidal composition diluted for application is normally in the range of about 0.001% to about 8% by weight. Many variations of spraying and dusting compositions known in the art may be used by substituting the esters of this invention into compositions known or apparent to the art.

The insecticidal or acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally or acaricidally effective amount of 2,2'-bridged[1,1'-biphenyl]-3-ylmethyl carboxylate be applied to the locus where control is desired. When the locus is soil, e.g., soil in which agricultural crops are planted, the active compound may be applied to and optionally incorporated into the soil. For most applications, an insecticidally or acaricidally effective amount will be about 75 to 4000 g per hectare, preferably 150 g to 3000 g per hectare.

The insecticidal and acaricidal activity of the 2,2'-bridged[1,1'-biphenyl]-3-ylmethyl carboxylates, whose preparation is described above, were evaluated as follows:

The activity was evaluated in topical application to southern armyworm (*Spodoptera eridania*), Mexican bean beetle (*Epilachna varivestis*), large milkweed bug (*Oncopeltus fasciatus*), cabbage looper (*Trichoplusia ni*), southern corn rootworm (*Diabrotica undecimpunctata*), and tobacco budworm (*Heliothis virescens*). Two replicates of 10 test larvae per replicate were placed in 9 cm petri dishes, each lined with a piece of filter paper and a food source. On the second or third dorsal thoracic segment of each larva was placed a 1 microliter droplet containing the desired amount of the test compound in acetone. The toxic effect of the compound was determined 24 hours after application. An insect was considered dead if it could no longer right itself and move in an oriented pattern. The results of these tests appear in Table 1.

The compounds were also tested in foliar applications at various concentrations in aqueous solutions containing 10% acetone and 0.25% emulsifier. The plants (English fava bean for pea aphid and pinto bean for the remaining species) were placed on a revolving turntable in a hood, and the test solutions were applied with a sprayer. The test solutions were applied to the upper and lower surfaces of the plant leaves while the turntable revolved 10 times (5 for upper surface and 5 for lower surface). The total spray time was approximately one minute, and the leaves were covered to runoff. In every case the lowest rate was applied first and the highest rate last. The plants were then allowed to dry. The treated leaves were removed and placed in 240 ml or 480 ml wax treated containers. Ten individuals of the appropriate species were placed in each container and the container capped. Mortality was read 48 hours post-treatment unless otherwise noted. Two replicates of ten individuals were made at each rate. Foliar evaluation used southern armyworm (*Spodoptera eridania*), Mexican bean beetle (*Epilachna varivestis*), pea aphid (*Acyrthosiphon pisum*), and twospotted spider mite (*Tetranychus urticae*). The results of the foliar tests appear in Table 2.

Several of the compounds were tested for activity against southern corn rootworm (*Diabrotica undecimpunctata*) following incorporation of the compounds into soil as follows: 33 ml of topsoil was placed in 120 ml plastic cups. The topsoil in each cup was treated with 5 ml of a test solution containing candidate insecticide in 10% acetone-water and a small amount of octylphenoxypolyethoxy ethanol. The test solution was stirred and incorporated into the topsoil to give a final concentration of test compound in the range 0.01–40 ppm (wt/wt). Each cup was capped with a plastic lid and stored for 14, 21, or 42 days. The treated soil was then infested with ten southern corn rootworm larvae, along with a kernel of germinating corn as a food source. The recapped cups were returned to storage for three days, after which time the percent mortality was determined. The results appear in Table 3.

TABLE 1

Topical Evaluation

| Compound | Insects[a] | | | | | |
|---|---|---|---|---|---|---|
| | SAW[b] LD$_{50}$ | MWB[b] LD$_{50}$ | MBB[b] LD$_{50}$ | CL[b] LD$_{50}$ | TBW[b] LD$_{50}$ | SCR[b] LD$_{50}$ |
| Ex. I (cis) | 121 | 176 | 64 | 241 | 193 | |
| Ex. II (cis) | 36 | 170 | 9.4 | 61 | 45 | 7.4 |
| Ex. III (cis) | 96 | 104 | 11 | 62 | 375 | 11.3 |
| Ex. III (trans) | 95 | 315 | 50 | 92 | 355 | 16.6 |
| Ex. IV (cis) | 54 | 83 | 4.26 | 64 | 212 | 3.7 |
| Ex. V (cis) | 460 | | 3320 | | | |
| Ex. VI (cis) | 1160 | | 762 | | | 2770 |
| Ex. VII (cis) | 410 | 396 | 20.6 | | | 11.4 |
| Ex. VIII (1R, cis) | 201 | 460 | | | | d |
| Ex. IX | 4600 | | 143 | | | 14.4 |
| Ex. X | | | 31.8 | | | 6.5 |
| Ex. XI (1R, cis) | 10.6 | 29.8 | 8 | 48.9 | 85 | 46.9 |
| Ex. XII (1R, cis) | 22.2 | 42.8 | 15.8 | 51.4 | | 6.8 |
| Ex. XIII (1R, trans) | 485 | 81.9 | 71.5 | | | 9.2 |
| Ex. XIV (1R, cis) | 48.8 | 280 | 32 | 104 | 164 | 3.2 |
| Ex. XV | 56.8 | 385 | 35.6 | 262 | | 63.1 |
| Ex. XVI | | 1085 | 67 | | | 104 |
| Ex. XVII | 454 | 288 | 91.2 | | | 333 |
| Ex. XVIII (cis) | 65.4 | 349 | 11.5 | 268 | 503 | 4 |
| Ex. XIX (1R, cis) | 63.3 | 735 | | 179 | 499 | 8.7 |
| Ex. XX (1R, cis) | 19.8 | 225 | | 15.5 | 41.3 | 1.3 |
| Ex. XXI (1S, cis)[e] | | | | | | |
| Ex. XXII (1R) | 1213 | | | | | 15 |

TABLE 1-continued

Topical Evaluation

| Compound | Insects[a] | | | | | |
|---|---|---|---|---|---|---|
| | SAW[b] LD50 | MWB[b] LD50 | MBB[b] LD50 | CL[b] LD50 | TBW[b] LD50 | SCR[b] LD50 |
| Ref.[c] | 27 | 620 | 18 | 560 | | 2330 |

[a] SAW = Southern armyworm
MWB = Milkweed bug
MBB = Mexican bean beetle
CL = Cabbage looper
TBW = Tobacco budworm
SCR = Southern corn rootworm
[b] ng/insect
[c] Data for [(1,1'-biphenyl)-3-yl]methyl cis-3-(2,2-dichloroethenyl)-2,2-dimethylcyclopropanecarboxylate. For comparison only. Compound not within scope of this invention.
[d] 100% kill at 2500 ng/insect
[e] No control at 2500 ng when applied to MBB, MWB, SAW; no control at 800 ng when applied to SCR.

TABLE 2

Foliar Evaluation

| Compound | Concentration (ppm) | Mortality (% killed)[a] | | | |
|---|---|---|---|---|---|
| | | SAW | MBB | PA | TSM |
| Ex. I (cis) | 80 | 80 | 75 | | |
| | 32 | 30 | 35 | 90 | |
| | 16 | 10 | 30 | 55 | |
| Ex. II (cis) | 32 | 95 | | | 78 |
| | 10 | | | 85 | |
| | 8 | 30 | 90 | | |
| Ex. III (cis) | 10 | 40 | 85 | 90 | 13 |
| | 4.5 | 5 | 55 | 55 | |
| Ex. III (trans) | 16 | 100 | 55 | 90 | |
| | 4 | 10 | 20 | 80 | |
| Ex. IV (cis) | 10 | 75 | | | 100 |
| | 2.1 | | 100 | | 4 |
| | 0.25 | | | 80 | |
| Ex. V (cis) | 500 | 100 | | 90 | 0 |
| | 64 | 0 | 0 | 30 | |
| Ex. V (trans) | 500 | 25 | | 0 | 0 |
| | 64 | 0 | 15 | 20 | |
| Ex. VI (cis) | 500 | 100 | | 90 | 0 |
| | 64 | 95 | 0 | 50 | |
| Ex. VII (cis) | 16 | | | | 24 |
| | 4 | | 95 | 0 | |
| Ex. VIII (1R, cis) | 16 | | | | 14 |
| | 4 | | 50 | 0 | |
| Ex. IX | 64 | | 100 | 75 | 0 |
| | 16 | | 70 | 50 | 0 |
| Ex. X | 64 | 0 | 50 | 70 | 33 |
| | 16 | 0 | 45 | 58 | 0 |
| Ex. XI (1R, cis) | 500 | 100 | | 95 | 100 |
| | 64 | | 100 | | |
| | 16 | | 90 | | |
| Ex. XII (1R, cis) | 500 | 100 | | 100 | 70 |
| | 64 | | 100 | 100 | 44 |
| | 16 | | 100 | 90 | 35 |
| Ex. XIII (1R, trans) | 500 | 100 | | 100 | 70 |
| | 64 | | 100 | 85 | 0 |
| | 16 | | 50 | 80 | 0 |
| Ex. XIV (1R, cis) | 500 | 100 | | 100 | 100 |
| | 64 | | 100 | 75 | 0 |
| | 16 | | 80 | 75 | 0 |
| Ex. XV | 500 | 100 | | 100 | 100 |
| | 64 | | 70 | 55 | 0 |
| | 16 | | 20 | 40 | 0 |
| Ex. XVI | 500 | 100 | | 100 | 95 |
| | 64 | | 95 | 45 | 0 |
| | 16 | | 55 | 5 | 0 |
| Ex. XVII | 500 | 100 | | 100 | 70 |
| | 64 | | 60 | 50 | 0 |
| | 16 | | 0 | 15 | 0 |
| Ex. XVIII (cis) | 500 | 100 | | 100 | 100 |
| | 64 | | 100 | 70 | 98 |
| | 16 | | 100 | 60 | 88 |
| Ex. XIX (1R, cis) | 1250 | 100 | | 100 | 0 |
| | 64 | | 100 | 85 | |
| | 16 | | 50 | 35 | |
| Ex. XX (1R, cis) | 1250 | 100 | 100 | 100 | 100 |
| | 64 | 100 | 100 | 95 | 100 |
| | 16 | 100 | 100 | 60 | 100 |
| Ex. XXI (1S, cis) | 1250 | 0 | 0 | 0 | 70 |
| Ex. XXII (1R) | 1250 | 100 | 100 | 100 | 100 |
| Ref.[b] | 500 | | | | 33 |
| | 32 | | 50 | 70 | |
| | 4 | 90 | | | |

[a] SAW = Southern armyworm
MBB = Mexican bean beetle
PA = Pea aphid
TSM = Twospotted spider mite
[b] Data for [(1,1'-biphenyl)-3-yl]methyl cis-3-(2,2-dichloroethenyl)-2,2-dimethylcyclopropanecarboxylate. For comparison only. Compound not within scope of this invention.

TABLE 3

Soil Incorporated Tests Against Southern Corn Rootworm

| Compound | Rate (ppm) | % Kill | | |
|---|---|---|---|---|
| | | 14 day | 21 day | 42 day |
| Ex. VII (cis) | 20 | | | 0 |
| | 10 | 100 | 0 | |
| Ex. VIII (1R, cis) | 20 | | | 35 |
| | 10 | 100 | 15 | 15 |
| | 5 | | 0 | 0 |
| Ex. IX | 10 | 25 | | |
| Ex. X | 10 | 5 | | |
| Ex. XI (1R, cis) | 20 | | | 90 |
| | 10 | 65 | 50 | |
| | 5 | | 25 | 15 |
| | 2.5 | | 20 | 5 |
| Ex. XII (1R, cis) | 10 | 70 | 100 | 100 |
| | 5 | | 65 | 90 |
| | 2.5 | | 35 | 40 |
| Ex. XIII (1R, trans) | 10 | 0 | | |
| Ex. XIV (1R, cis) | 10 | 75 | | |
| | 8 | | 45 | 55 |
| | 4 | | 40 | 45 |
| | 2 | | 35 | 35 |
| Ex. XV | 10 | 20 | | |
| Ex. XVI | 10 | 0 | | |
| Ex. XVII | 10 | 25 | | |
| Ex. XVIII (cis) | 10 | 95 | | |
| | 8 | | 60 | |
| | 4 | | 40 | 40 |
| | 2 | | | 25 |
| Ex. XIX (1R, cis)[a] | 10 | 0 | | |
| Ex. XX (1R, cis)[b] | 10 | | | |

[a] 20% kill when treated soil was infested immediately after treatment.
[b] 100% kill when treated soil was infested immediately after treatment.

I claim:

1. Insecticidal and acaricidal 2,2'-bridged[1,1'-biphenyl]-3-ylmethyl pyrethroid esters of the formula

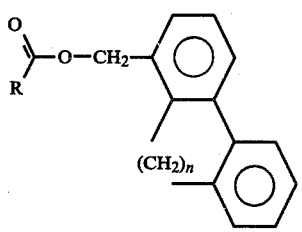

wherein n is 1–4 and R is selected from 3-(2,2-dihaloethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(2- chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 3-(1,2,2,2-tetrabromoethyl)-2,2-dimethylcyclopropyl; 2,2-dichloro-1-(4-ethoxyphenyl)-cyclopropyl; 2-(2-chloro-α,α,α-trifluoro-p-toluidino)-3-methylbutyl; and 4-chloro-α-(1-methylethyl)phenylmethyl.

2. A compound of claim 1 wherein R is 3-(2,2-dichloroethenyl)-2,2-dimethylcyclopropyl or 3-(2-chloro-3,3,3-trifluoromethyl-1-propenyl)-2,2-dimethylcyclopropyl.

3. A compound of claim 2 wherein R is a cis isomer.

4. A compound of claim 1 wherein n is 2 or 3.

5. (6,7-Dihydro-5H-dibenzo[a,c]cyclohepten-4-yl)methyl 3-(2,2-dichloroethenyl)-2,2-dimethylcyclopropanecarboxylate.

6. (6,7-Dihydro-5H-dibenzo[a,c]cyclohepten-4-yl)methyl 3-(2-chloro-3,3,3-trifluoropropenyl)-2,2-dimethylcyclopropanecarboxylate.

7. The compound of claim 6 which is the 1R,cis isomer.

8. (9,10-Dihydro-1-phenanthryl)methyl 3-(2,2-dichloroethenyl)-2,2-dimethylcyclopropanecarboxylate.

9. (9,10-Dihydro-1-phenanthryl)methyl 3-(2-chloro-3,3,3-trifluoropropenyl)-2,2-dimethylcyclopropanecarboxylate.

10. (5,6,7,8-Tetrahydrodibenzo[a,c]cycloocten-4-yl)methyl 3-(2,2-dichloroethenyl)-2,2-dimethylcyclopropanecarboxylate.

11. (5,6,7,8-Tetrahydrodibenzo[a,c]cycloocten-4-yl)methyl 3-(2-chloro-3,3,3-trifluoropropenyl)-2,2-dimethylcyclopropanecarboxylate.

12. (6,7-Dihydro-5H-dibenzo[a,c]cyclohepten-4-yl)methyl 2,2-dichloro-1-(4-ethoxyphenyl)cyclopropanecarboxylate.

13. (6,7-Dihydro-5H-dibenzo[a,c]cyclohepten-4-yl)methyl 2-(2-chloro-α,α,α-trifluoro-p-toluidino)-3-methylbutyrate.

14. (6,7-Dihydro-5H-dibenzo[a,c]cyclohepten-4-yl)methyl 3-(2,2-dibromoethenyl)-2,2-dimethylcyclopropanecarboxylate.

15. The compound of claim 14 which is the 1R,cis isomer.

16. (6,7-Dihydro-5H-dibenzo[a,c]cyclohepten-4-yl)methyl 3-(cyclopentylidenemethyl)-2,2-dimethylcyclopropanecarboxylate.

17. (6,7-Dihydro-5H-dibenzo[a,c]cyclohepten-4-yl)methyl 3-(1,2-dibromo-2,2-dichloroethyl)-2,2-dimethylcyclopropanecarboxylate.

18. The compound of claim 17 which is the 1R,cis isomer.

19. (6,7-Dihydro-5H-dibenzo[a,c]cyclohepten-4-yl)methyl 2,2,3,3-tetramethylcyclopropanecarboxylate.

20. (6,7-Dihydro-5H-dibenzo[a,c]cyclohepten-4-yl)methyl α-(1-methylethyl)-4-chlorobenzeneacetate.

21. (6,7-Dihydro-5H-dibenzo[a,c]cyclohepten-4-yl)methyl 2,2-dichloro-3,3-dimethylcyclopropanecarboxylate.

22. (6,7-Dihydro-5H-dibenzo[a,c]cyclohepten-4-yl)methyl 3-(3-chloro-2,3,3-trifluoro-1-propenyl)-2,2-dimethylcyclopropanecarboxylate.

23. The compound of claim 22 which is the cis isomer.

24. (6,7-Dihydro-5H-dibenzo[a,c]cyclohepten-4-yl)methyl 3-(1,2,2,2-tetrabromoethyl)-2,2-dimethylcyclopropanecarboxylate.

25. An insecticidal or acaricidal composition comprising in admixture with an agriculturally acceptable carrier an insecticidally or acaricidally effective amount of at least one compound of the formula

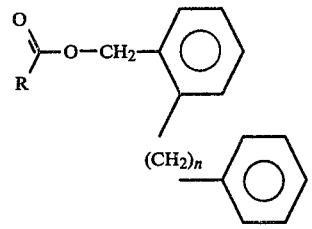

wherein n is 1–4 and R is selected from 3-(2,2-dihaloethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 3-(1,2,2,2-tetrabromoethyl)-2,2-dimethylcyclopropyl; 2,2-dichloro-1-(4-ethoxyphenyl)-cyclopropyl; 2-(2-chloro-α,α,α-trifluoro-p-toluidino)-3-methylbutyl; and 4-chloro-α-(1-methylethyl)phenylmethyl.

26. A method of controlling insects or acarids which comprises applying to the locus where control is desired an insecticidally or acaricidally effective amount of at least one compound of the formula

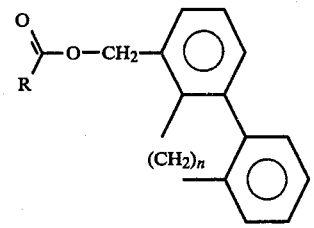

wherein n is 1–4 and R is selected from 3-(2,2-dihaloethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 3-(1,2,2,2-tetrabromoethyl)-2,2-dimethylcyclopropyl; 2,2-dichloro-1-(4-ethoxyphenyl)-cyclopropyl; 2-(2-chloro-α,α,α-trifluoro-p-toluidino)-3-methylbutyl; and 4-chloro-α-(1-methylethyl)phenylmethyl.

27. The method of claim 26 wherein the locus is soil and the compound is incorporated into the soil.

28. The method of claim 27 wherein the compound is selected from (5,6,7,8-tetrahydrodibenzo[a,c]cycloocten-4-yl)methyl 3-(2-chloro-3,3,3-trifluoropropenyl)-2,2-dimethylcyclopropanecarboxylate, (5,6,7,8-tetrahydrodibenzo[a,c]cycloocten-4-yl)methyl 3-(2,2-dichloroethenyl)-2,2-dimethylcyclopropanecarboxylate, (6,7-dihydro-5H-dibenzo[a,c]cyclohepten-4-yl)methyl 2,2-dichloro-1-(4-ethoxyphenyl)cyclopropanecarboxylate, (6,7-dihydro-5H-dibenzo[a,c]cyclohepten-4-yl)methyl 2-(2-chloro-α,α,α-trifluoro-p-toluidino)-3-methylbutyrate, (6,7-dihydro-5H-dibenzo[a,c]cyclohepten-4-yl)methyl 3-(2,2-dichloroethenyl)-2,2-dimethylcyclopropanecarboxylate, (6,7-dihydro-5H-dibenzo[a,c]cyclohepten-4-yl)methyl 3-(2,2-dibromoethenyl)-2,2-dimethylcyclopropanecarboxylate, (6,7-dihydro-5H-dibenzo[a,c]cyclohepten-4-yl)methyl 3-(1,2-dibromo-2,2-dichloroethyl)-2,2-dimethylcyclopropanecarboxylate, (6,7-dihydro-5H-dibenzo[a,c]cyclohepten-4-yl)methyl 2,2,3,3-tetramethylcyclopropanecarboxylate, (6,7-dihydro-5H-dibenzo[a,c]cyclohepten-4-yl)methyl 2,2-dichloro-3,3-dimethylcyclopropanecarboxylate, (6,7-dihydro-5H-dibenzo[a,c]cyclohepten-4-yl)methyl 3-(3-chloro-2,3,3-trifluoro-1-propenyl)-2,2-dimethylcyclopropanecarboxylate, and (6,7-dihydro-5H-dibenzo[a,c]cyclohepten-4-yl)methyl 3-(2-chloro-3,3,3-trifluoro-1-propenyl)-2,2-dimethylcyclopropanecarboxylate.

29. The method of claim 27 wherein the compound is (5,6,7,8-tetrahydrodibenzo[a,c]cycloocten-4-yl)methyl 1R,cis-3-(2,2-dichloroethenyl)-2,2-dimethylcyclopropanecarboxylate.

30. The method of claim 27 wherein the compound is (6,7-dihydro-5H-dibenzo[a,c]cyclohepten-4-yl)methyl 1R,cis-3-(2,2-dichloroethenyl)-2,2-dimethylcyclopropanecarboxylate.

31. The method of claim 27 wherein the compound is (6,7-dihydro-5H-dibenzo[a,c]cyclohepten-4-yl)methyl 1R,cis-3-(2,2-dibromoethenyl)-2,2-dimethylcyclopropanecarboxylate.

32. The method of claim 27 wherein the compound is (6,7-dihydro-5H-dibenzo[a,c]cyclohepten-4-yl)methyl 1R,cis-3-(1,2-dibromo-2,2-dichloroethyl)-2,2-dimethylcyclopropanecarboxylate.

33. The method of claim 27 wherein the compound is (6,7-dihydro-5H-dibenzo[a,c]cyclohepten-4-yl)methyl cis-3-(3-chloro-2,3,3-trifluoro-1-propenyl)-2,2-dimethylcyclopropanecarboxylate.

34. The method of claim 27 wherein the compound is (6,7-dihydro-5H-dibenzo[a,b]cyclohepten-4-yl)methyl cis-3-(2-chloro-3,3,3-trifluoro-1-propenyl)-2,2-dimethylcyclopropanecarboxylate.

35. The method of claim 27 wherein the compound is (6,7-dihydro-5H-dibenzo[a,c]cyclohepten-4-yl)methyl 1R,cis-3(2-chloro-3,3,3-trifluoro-1-propenyl)-2,2-dimethylcyclopropanecarboxylate.

* * * * *

UNITED STATES PATENT AND TRADEMARK OFFICE
CERTIFICATE OF CORRECTION

PATENT NO. : 4,451,484
DATED : May 29, 1984
INVENTOR(S) : Ernest L. Plummer

It is certified that error appears in the above—identified patent and that said Letters Patent is hereby corrected as shown below:

Col. 1, line 67, "3-methyl" should read --3-ylmethyl--.
Col. 8, line 49, "5e,uns/H/" should read --5H--;
       line 60, "5e,uns/H/" should read --5H--;
       line 63, "5e,uns/H/" should read --5H--.
Col. 23, line 67, "claim; 22" should read --claim 22--.
Col. 24, claim 25, formula is incomplete. Correction below.

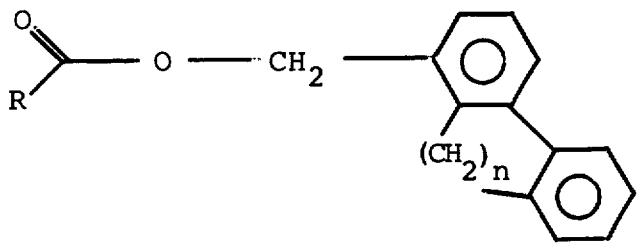

Signed and Sealed this

Eighteenth Day of June 1985

[SEAL]

Attest:

DONALD J. QUIGG

Attesting Officer    Acting Commissioner of Patents and Trademarks